United States Patent [19]

Wagnon et al.

[11] Patent Number: 4,746,648

[45] Date of Patent: May 24, 1988

[54] PEPTIDE DERIVATIVES WHICH INHIBIT RENIN AND ACID PROTEASES

[75] Inventors: Jean Wagnon; Georges Callet, both of Montpellier; Jean-Pierre Gagnol, Saint Martin de Londres; Dino Nisato, Saint Georges D'Orques; Catherine Cazaubon, Montpellier, all of France

[73] Assignee: Institut National de la Recherche Medicale Sanofi, France

[21] Appl. No.: 826,375

[22] Filed: Feb. 5, 1986

[30] Foreign Application Priority Data

Feb. 12, 1985 [FR] France .................. 85 01981
Feb. 12, 1985 [FR] France .................. 85 01982

[51] Int. Cl.$^4$ .................. A61K 37/43; C07K 5/02; C07K 7/06

[52] U.S. Cl. .................. 514/17; 530/330; 530/332

[58] Field of Search .................. 530/332, 329, 330; 514/17, 18, 19

[56] References Cited

FOREIGN PATENT DOCUMENTS 0081783 6/1983 European Pat. Off. .
2531951 2/1984 France .

Primary Examiner—Delbert R. Phillips
Attorney, Agent, or Firm—Bacon & Thomas

[57] ABSTRACT

The invention relates to peptide derivatives modeled on the basis of pepstatin.

These derivatives inhibit renin and acid proteases.

7 Claims, No Drawings

PEPTIDE DERIVATIVES WHICH INHIBIT RENIN AND ACID PROTEASES

The present invention relates to new peptide derivatives which inhibit renin and acid proteases. It also relates to a process for their preparation and their application in therapy.

In 1970, UMEZAWA isolated a pentapeptide from a culture of streptomyces; this pentapeptide was called pepstatin and its structure was subsequently established and corresponds to the formula:

isovaleryl-L-valyl-L-valyl-statyl-L-alanyl-statin in which the name "statin" denotes the uncommon amino acid (3S,4S)-4-amino-3-hydroxy-6-methylheptanoic acid.

It has been shown that pepstatin inhibits acid proteases and is active especially against pepsin, cathepsin D and renin. In particular, renin, an enzyme originating from the kidney, is involved in the sequence angiotensinogen-angiotensin I-angiotensin II in the conversion of angiotensinogen to angiotensin.

As a powerful vasoconstrictor, angiotensin II plays a part in regulating the arterial pressure. The possibility of using pepstatin to combat arterial hypertension in man has been considered. However, since pepstatin acts on all acid proteases and has a low solubility in aqueous media and a low affinity for renin, its use in therapy has proved difficult. Pepstatin derivatives have been described in the scientific literature. For example, attempts have been made to solubilize pepstatin by lengthening the peptide chain (J. Cardiovasc. Pharmacol., 1980, 2, 687–698).

By contrast, the present invention relates to peptides modeled on the basis of pepstatin. In certain cases, the introduction of unnatural amino acids makes it possible to increase the solubility of these compounds and their resistance to proteolysis. Totally surprisingly, it has been found that the peptides according to the invention, which carry hydrophilic residues at various sites, have a high level of activity which is greatly superior to that of pepstatin as an inhibitor of human renin.

The present invention relates to peptides having a high level of activity as inhibitors of renin and other acid proteases.

The following abbreviations will be used in the present description and in the claims:

Amino acids and protecting or activating groups

These abbreviations are consistent with those indicated by the Nomenclature Commission of IUPAC-IUB, Biochemistry Section. The most recent recommendations are reported in Eur. J. Biochem., 1984, 138, 5-7 and 9-37.

Amino acids and derivatives

Ala: alanine
Asn: asparagine
Asp: aspartic acid
Gln: glutamine
Gly: glycine
His: histidine
Ile: isoleucine
Leu: leucine
Met: methionine
Nle: norleucine
Nva: norvaline
Phe: phenylalanine
Ser: serine
Sta: statin
AHPPA: 4-amino-3-hydroxy-5-phenylpentanoic acid
ACHPA: 4-amino-5-cyclohexyl-3-hydroxypentanoic acid
Met($O_2$): methionine dioxide
(PhCH$_2$)Asp: O-benzylaspartic acid
Abu: 2-aminobutyric acid
(Pyr-2)Ala: (pyridin-2-yl)alanine

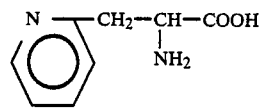

(Pyr-3)Ala: (pyridin-3-yl)alanine
(Pyr-4)Ala: (pyridin-4-yl)alanine
(tauMe)His: (tele-methyl)histidine

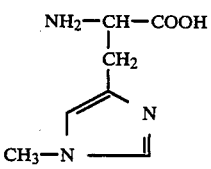

(tauEt)His: (tele-ethyl)histidine
(piMe)His: (pros-methyl)histidine

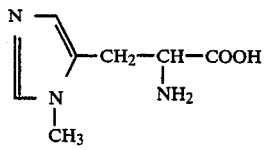

(2-methylthiazol-4-yl)Gly:

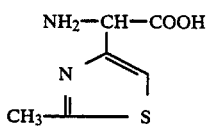

(1-methylimidazol-2-yl)Ala:

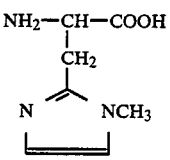

Hph: homophenylalanine
Phg: phenylglycine
Cpg: cyclopentylglycine
(CH$_3$CH$_2$O)Ser: ethyl ether of serine
((CH$_3$)$_3$CO)Ser: t-butyl ether of serine
(PhCH$_2$O)Ser: benzyl ether of serine
((Pyr-2)CH$_2$O)Ser: (pyridin-2-yl)methyl ether of serine
(Pentyl)Ala: 2-aminooctanoic acid
(Ph)Gln: N-phenylglutamine
(Ph)Asn: N-phenylasparagine Unless indicated otherwise, these amino acids have the L configuration.

Unless indicated otherwise, Sta, AHPPA and ACHPA have the 3S,4S configuration.

Protecting and activating groups

Ac: acetyl
Boc: t-butoxycarbonyl
(Boc)$_2$O: bis(tert.-butoxycarbonic)anhydride
HONSu: N-hydroxysuccinimide
OEt: ethyl ester
OMe: methyl ester
ONp: p-nitrophenyl ester
ONSu: N-hydroxysuccinimide ester
OTcp: 2,4,5-trichlorophenyl ester
iVa: isovaleryl
Z: benzoyloxycarbonyl The following abbreviations will also be used:

AcOEt: ethyl acetate
AcOH: acetic acid
Bop: benzyloxytrisdimethylaminophosphonium hexafluorophosphate
TLC: thin layer chromatography
DCCI: dicyclohexylcarbodiimide
DCHA: dicyclohexylamine
DCU: dicyclohexylurea
DIPEA: diisopropylethylamine
DMF: dimethylformamide
DMSO: dimethyl sulfoxide
Ether: ethyl ether
HOBt: 1-hydroxybenzotriazole
KHSO$_4$—K$_2$SO$_4$: aqueous solution containing 16.6 g of potassium bisulfate and 33.3 g of potassium sulfate per liter
MeOH: methanol
NEM: N-ethylmorpholine
NMM: N-methylmorpholine
RT: room temperature
TFA: trifluoroacetic acid
min: minutes
h: hours The compounds according to the invention correspond to the following general formula:

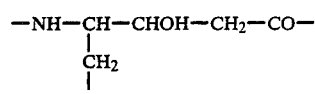

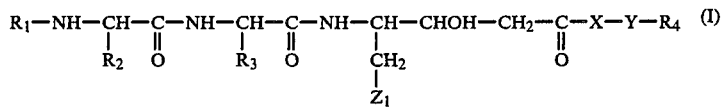

in which:

R$_1$ represents an acyl group chosen from the following groups: alkylcarbonyl, alkoxycarbonyl, arylcarbonyl, arylalkylcarbonyl, arylalkoxycarbonyl, heterocyclylcarbonyl, heterocyclylalkylcarbonyl, in which the alkyl group is optionally substituted by a hydroxyl group, heterocyclylcarbonylalkylcarbonyl, heterocyclylalkenylcarbonyl and cycloalkylcarbonyl, or represents a (lower alkyl)sulfonyl group which is unsubstituted or substituted on the alkyl by a free amino group or an amino group carrying a protecting group, or by a phenyl, or represents a phenylsulfonyl group which is unsubstituted or substituted on the phenyl nucleus by a lower alkyl;

R$_2$ represents a lower alkyl group which is unsubstituted or substituted by phenyl, naphthyl, cyclohexyl or pyridyl, or R$_2$ represents a phenyl, naphthyl, cyclohexyl or pyridyl radical;

R$_3$ represents hydrogen, a lower alkenyl, a phenyl, a naphthyl, a cycloalkyl containing 3 to 6 carbon atoms, a 5-membered or 6-membered monocyclic heterocyclic group which is unsubstituted or substituted by a lower alkyl or trifluoromethyl, or alternatively a lower alkyl substituted by a di(lower alkyl)amino group, by a carboxyl esterified by a lower alkyl or a benzyl, by a free carbamoyl or a carbamoyl substituted by one or two lower alkyls or by a phenyl, by a lower alkoxy or benzyloxy group, by a pyridylmethoxy group, by a (lower alkyl)sulfinyl or (lower alkyl)sulfonyl group, by a cycloalkyl containing from 3 to 6 carbon atoms or by a 5-membered or 6-membered monocyclic heterocyclic group which is unsubstituted or substituted by a lower alkyl or a trifluoromethyl, with the proviso that R$_3$ is not the (imidazol-4-yl)methyl group;

R$_4$ represents a hydroxyl, a lower alkoxy, a benzyloxy or a free amino group or an amino group substituted by one or 2 lower alkyls;

Z$_1$ represents isopropyl, phenyl or cyclohexyl, respectively forming with the radical:

$$-NH-CH-CHOH-CH_2-CO-$$
$$\phantom{-NH-}|$$
$$\phantom{-NH-}CH_2$$
$$\phantom{-NH-}|$$

the residue of the amino acid statin, namely (3S,4S)-4-amino-3-hydroxy-6-methylheptanoic acid, of (3S,4S)-4-amino-3-hydroxy-5-phenylpentanoic acid (AHPPA) or of (3S,4S)-4-amino-5-cyclohexyl-3-hydroxypentanoic acid (ACHPA); and·

X-Y is a dipeptide chosen from the group comprising Ala-Sta, Ala-Leu, Leu-Phe, Val-Sta, Abu-Sta, Ile-Ser and Phg-Sta.

The present invention also includes any pharmaceutically acceptable salts of the peptides of the formula (I) with mineral or organic acids or alkali metals or alkaline earth metals.

The term "alkyl" denotes saturated or unsaturated aliphatic hydrocarbon radicals containing 1 to 10 carbon atoms. The preferred "alkyl" groups for the purposes of the invention are the lower alkyl groups such as defined below.

The expressions "lower alkyl", "lower alkenyl" and "lower alkylidene", as used here, denote saturated or unsaturated aliphatic hydrocarbon radicals containing up to 6 carbon atoms.

The expression "lower alkoxy" represents the hydroxyl group substituted by a lower alkyl group such as defined above.

The expression "5-membered or 6-membered monocyclic heterocycle" includes pyrrolidine, imidazole, thiazole, thiophene, furan, pyrrole, triazole, oxazole, isoxazole, pyridine and thiadiazoles.

The expression "protecting group" is understood as meaning a protecting group normally used in peptide chemistry, for example Boc, Z or iVa.

The expression "acyl group" used to define R$_1$ includes the residues of aliphatic, alicyclic, aromatic or heterocyclic carboxylic acids. Preferred acyl groups are the residue of esterified carbonic acid, especially the groups Boc and Z, the residue of alkanoic acids containing from 2 to 6 carbon atoms, especially the group iVa, the residue of cyclohexylcarboxylic acid, the residue of phenylaliphatic acids, especially the phenylacetyl, 3-phenylpropionyl and dibenzylacetyl groups, the residue of arylcarboxylic acids, such as naphthoic acid, biphenylcarboxylic acid and benzoic acid which is unsubstituted or substituted on the phenyl nucleus, especially the benzoyl group, the residue of a carboxylic acid in which the carboxyl is bonded to a 5-membered or 6-membered monocyclic heterocycle, especially the piperidinylcarboxylic groups, the picolinoyl, nicotinoyl and isonicotinoyl groups, and the residue of alkanoic or alkenoic acids, such as acetic acid, propionic acid, butyric acid, valeric acid and their omega-hydroxy or omega-oxa derivatives substituted in the omega position by a 5-membered or 6-membered monocyclic heterocycle as exemplified above.

More particularly, the present invention relates preferentially to the peptide derivatives of the formula (I) in which $R_2$, $R_3$, $R_4$, X, Y and $Z_1$ are as defined above and $R_1$ represents one of the following groups:

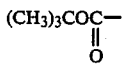

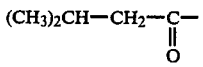

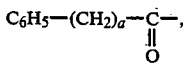

in which a=0, 1 or 2

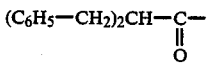

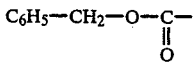

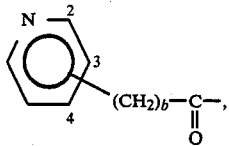

in which b=0, 1, 2, 3, 4, 5 or 6

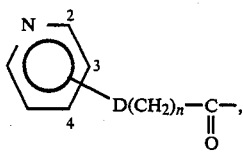

in which D=

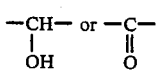

and n=1, 2, 3, 4 or 5

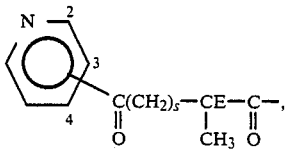

in which E=—H or —CH$_3$ and s=1, 2, 3 or 4

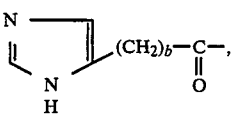

in which b=0, 1, 2, 3, 4, 5 or 6

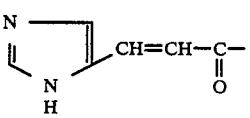

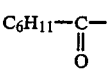

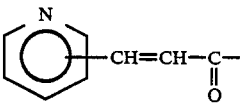

NH$_2$CH$_2$CH$_2$—SO$_2$—
BocNHCH$_2$CH$_2$—SO$_2$—
ZNHCH$_2$CH$_2$—SO$_2$—
A—SO$_2$—, in which A is a lower alkyl
C$_6$H$_5$—(CH$_2$)$_a$—SO$_2$—, in which a=0, 1 or 2

Particular preference is given to the peptide derivatives of the formula (I) in which $R_2$, $R_3$, $R_4$, X, Y and $Z_1$ are as defined above and $R_1$ represents an acyl group chosen from:
isovaleryl,
4-(pyridin-2-yl)-4-oxobutyryl,
4-(pyridin-2-yl)-4-hydroxybutyryl,
3-(pyridin-3-yl)propionyl,
4-(pyridin-3-yl)butyryl,
nicotinoyl and
benzenesulfonyl.

Particular preference is also given to the compounds of the formula (I) in which $R_1$, $R_2$, $R_4$, X, Y and $Z_1$ are as defined above and $R_3$ is such that the residue —NH—CH($R_3$)—CO— represents the residue (tauMe)His.

The products according to the invention can be prepared by the methods normally used in peptide chemistry. More particularly, starting from a compound of the formula:

H—Y—R'$_4$ in which R'$_4$ is a lower alkoxy, a benzyloxy or a free amino group or an amino group substituted by one or two lower alkyls, and Y is chosen from the residues of the amino acids Sta, Leu, Phe and Ser, the various amino acids, appropriately protected, are coupled in a step-wise fashion, the product obtained at each step being deprotected by known processes before being subjected to further coupling, and each of the coupling operations being carried out using either an activated ester of the amino acid to be coupled or the N-protected amino acid in the presence of dicyclohexylcarbodiimide. The starting material is advantageously a lower alkyl ester of the C-terminal amino acid with which the next amino acid in the sequence is condensed. After the amine group of the dipeptide has been freed, the peptide chain is lengthened by coupling with the next, appropriately protected amino acid. Each coupling phase is followed by a selective operation to free the amine which will take part in the reaction to create the next peptide link. The various coupling operations are carried out either using an activated ester of the amino acid to be coupled or using the N-protected amino acid in the presence of dicyclohexylcarbodiimide. Depending on the nature of the protecting group used, the phases involving selective deprotection of the amine are carried out either by hydrogenolysis or by acidolysis in a strong acid medium such as trifluoroacetic acid. If the amino acid to be introduced into the sequence has a reactive group in its side chain, the said group should be blocked by an appropriate protecting group, which is subsequently removed.

The protection of the initial amino acid by the group $R_1$ is carried out by known methods before the residue:

$R_1-NH-CHR_2-CO-$ is coupled with the next amino acid.

The residue $-NH-CHR_3-CO-$ is an unnatural amino acid prepared by known methods; it is then coupled with the next amino acid by the usual method.

The peptides (I) in the acid form ($R_4=OH$) can be obtained from the corresponding esters by saponification in a dilute alkaline medium. It is also possible to prepare their salts. The peptides (I) in the amide form ($R_4=NH_2$ or $R_4=N(Alk)_2$) are obtained directly by taking the commercially available amino amides as the starting materials.

According to the general scheme, it is possible either to prepare the whole of the desired sequence or to prepare 2 fragments of this sequence, which are finally coupled to give the desired peptide.

Any pharmaceutically acceptable salts of the peptides according to the invention with mineral or organic acids or alkali metals or alkaline earth metals are formed by conventional methods.

The compounds of the present invention have a very strong inhibitory action on human plasma renin activity, which in general is considerably greater than that of the natural product: pepstatin; in this capacity, they can be used in the treatment of arterial hypertension.

They also possess a marked inhibitory action on acid proteases, especially pepsin. It is therefore possible to consider using the products according to the invention in areas of therapy where the inhibition of such enzyme systems is justified; apart from arterial hypertension, particularly relevant areas are gastroduodenal ulcers and inflammatory complaints.

The present invention also relates to antihypertensive pharmaceutical compositions in which the peptides of the formula (I) or their pharmaceutically acceptable salts are present as active principles.

The peptides of the present invention can be administered in therapy by intravenous, intramuscular or subcutaneous injection. They are used in a solvent such as physiological serum (isotonic saline solution) or in a buffer such as phosphate buffer; they can also be suspended in a pharmaceutically acceptable aqueous or non-aqueous diluent. Each dosage unit can contain from 1 to 1000 mg of active principle.

The quantity of active principle to be used varies according to the desired therapeutic effects, the severity of the complaint to be treated and the chosen method of administration. It must be determined for each patient and is most commonly between 0.100 g and 2 g of active principle.

The non-limiting examples which follow are given in order to illustrate the present invention.

In all these examples, the pH of the solutions in an organic solvent is measured or monitored using wet pH indicator paper.

The indicated melting points (m.p.) are measured by the capillary tube method.

Finally, the nuclear magnetic resonance spectra were run at 250 MHz in DMSO solution with hexamethyldisiloxane as the internal standard.

The following abbreviations are used:
s: singlet
d: doublet
m: multiplet or unresolved signals
q: quadruplet
Further abbreviations used are:
H ar denotes aromatic H
H im denotes H of the imidazole
H pyr denotes H of the pyridine
The chemical shifts (delta) are measured in ppm.

EXAMPLE 1

Boc-Phe-(PhCH$_2$)Asp-Sta-Ala-Leu-OMe (SR 42926)

1. Boc-Ala-Leu-OMe 2.86 g of Boc-Ala-ONSu, 1.81 g of Leu-OMe.HCl and 1.15 g of NEM are dissolved successively in 50 ml of CH$_2$Cl$_2$ at RT. The pH is checked to see that it is 6–7; if not, it is adjusted by the addition of NEM. The organic solution is stirred for 4 hours at RT and then washed successively with 5% KHSO$_4$—K$_2$SO$_4$ solution, water and 5% NaHCO$_3$ solution; it is dried over Na$_2$SO$_4$ and the solvent is then evaporated off to give an oil.

Yield: 2.93 g (92%).

2. Ala-Leu-OMe.TFA 360 mg of the previous product are covered with 5 ml of TFA. After 20 min, the TFA is evaporated off and the residue is taken up by a mixture of equal volumes of pentane and ether. A white solid appears on scratching and is filtered off, rinsed with ether and dried.

Yield: 320 mg (85%).

3. Boc-Sta-Ala-Leu-OMe 330 mg of the previously obtained TFA salt are solubilized in 30 ml of dioxane containing 230 mg of NEM; 275 mg of Boc-Sta-OH, 206 mg of DCCI and 135 mg of HOBt are added, the pH is adjusted to a value of 6–7 with NEM if necessary and the mixture is then stirred for 24 hours at RT. The DCU is filtered off, the solvent is evaporated off, the residue is dissolved in a mixture of equal volumes of AcOEt and hexane and the solution is chromatographed on a column of Merck 60 silica gel in the same solvent mixture, elution being carried out with 250 ml of the same solvent mixture, then 250 ml of the mixture in proportions of 75/25 by volume, and then 100 ml of AcOEt. The fractions containing the product are evaporated and the residues are taken up in ether, filtered off and dried.

Yield: 380 mg (80%).

4. Boc-(PhCH₂)Asp-Sta-Ala-Leu-OMe 473 mg of the previously obtained peptide are treated with 8 ml of TFA at 0° C. for 15 min; the mixture is concentrated in vacuo at t=25° C., the concentrate is taken up with ether and the mixture is evaporated. This gives a solid which is taken up with $CH_2Cl_2$, the salt is neutralized in the cold with a slight excess of NMM, and 405 mg of Boc-(PhCH₂)Asp, 191 mg of HOBt and 258 mg of DCCI are then added. The pH is adjusted to 7 by the addition of NMM and the mixture is then stirred for 18 h. It is then washed with a solution of $KHSO_4$ (about 1M) and a solution of $NaHCO_3$ (about 1M), dried and concentrated. After chromatography on a silica column with AcOEt as the eluent, 169 mg of the expected product are obtained, which crystallizes on evaporation; m.p.=147°–149° C.

5. SR 42926

169 mg of the previous product are treated with 8 ml of TFA at 0° C. for 15 min. The mixture is concentrated in vacuo at 25° C., the concentrate is taken up with ether and the mixture is evaporated. This gives an oil which is taken up with $CH_2Cl_2$, and the salt is neutralized in the cold with a slight excess of NMM. A mixture of 100 mg of Boc-Phe-ONp, 38 mg of HOBt and 26 mg of NMM is stirred for 2 h in $CH_2CL_2$ and then added to the above salt. After stirring for 24 h, the organic phase is washed with a solution of $KHSO_4$ and a solution of $NaHCO_3$, dried and concentrated. After chromatography on silica (eluent: AcOEt), the expected product is obtained, which crystallizes on evaporation of the solvent.

Yield: 103 mg (50%); m.p.=154°–155° C.

NMR SPECTRUM

| Delta | Appearance | Protons | Assignment |
| --- | --- | --- | --- |
| 8.34–7.05 | m | 14 H | 4 NHCO<br>10 H ar |
| 6.86 | d, J = 8 Hz | 1 H | NHCO₂ |
| 5.04 | s | 2 H | CO₂C$\underline{H_2}$C₆H₅ |
| 3.55 | s | 3 H | OCH₃ |
| 2.20–2.00 | m | 2 H | CH₂CO (Sta) |
| 1.20 | s | 9 H | C(C$\underline{H_3}$)₃ |
| 1.13 | d, J = 7 Hz | 3 H | CH₃ (Ala) |
| 0.86–0.69 | m | 12 H | (C$\underline{H_3}$)₂CH |

EXAMPLE 2

Boc-Phe-(2-methylthiazol-4-yl)Gly-Sta-Ala-Leu-OMe (SR 43059)

1. Ethyl (R,S)-(2-methylthiazol-4-yl)glycinate

This product is prepared by the method described in J. Med. Chem., 1973, 16, 978–984.

2. Ethyl (R,S)-(2-methylthiazol-4-yl)-N-tert.-butoxycarbonyl-glycinate 6.5 g of the previously prepared compound are stirred for 3 days in 60 ml of water with 8.1 g of Boc₂O, 32.5 ml of dioxane and triethylamine to give an alkaline pH. The mixture is then concentrated at 30° C., the concentrate is taken up with ether and the mixture is washed with water and then with a solution of $KHSO_4$, water and a solution of $NaHCO_3$, dried and concentrated. This gives 8.5 g of a yellow oil.

3. (R,S)-(2-methylthiazol-4-yl)-N-tert.-butoxycarbonylglycine 4.5 g of the previously obtained compound are reacted in 80 ml of dioxane with 0.72 mg of sodium hydroxide dissolved in 15 ml of water. The reaction is followed by TLC. After 2 h, a further 0.6 g of sodium hydroxide in 2 ml of water is added. After 3 h 45 min, no more starting material is present. The pH is brought down to 5 with 15 ml of N HCl, the mixture is concentrated at 30° C., the concentrate is taken up with water, the mixture is acidified with $KHSO_4$ and extracted with AcOEt and the extract is washed with water, dried and concentrated. 2.7 g of a yellow powder are collected.

4. Boc-Sta-Ala-Leu-OMe

This peptide is prepared by the method described in Example 1.

5. (R,S)-Boc-(2-methylthiazol-4-yl)Gly-Sta-Ala-Leu-OMe 473 mg of the previous product are placed in 5 ml of TFA at 0° C. After 20 min, the mixture is concentrated, the concentrate is taken up 3 times with anhydrous ether and the mixture is then concentrated to minimum volume. The product obtained is dissolved in 20 ml of $CH_2Cl_2$ and the pH is brought to about 7 by the addition of DIPEA. 260 mg of the compound obtained in step 3 and 441 mg of Bop are then added. After stirring for 4 days at pH 7, the mixture is treated with an aqueous solution of sodium chloride and then with an aqueous solution of bicarbonate and with water, dried and concentrated, and the concentrate is then chromatographed on silica. By elution with AcOEt and then an AcOEt/MeOH mixture, 9/1 by volume, an amorphous solid fraction of 607 mg is collected by precipitation in pentane.

6. SR 43059

251 mg of the previously obtained compound are placed in 4 ml of TFA at 0° C. and are then treated in the usual way. The TFA salt obtained is placed in 15 ml of $CH_2Cl_2$, the reaction medium is brought to pH 7 by the addition of DIPEA, and 149 mg of Boc-Phe-ONp and 61.2 mg of HOBt are then added. After 24 hours, the mixture is washed in the same way as in the previous step and then chromatographed on silica, elution being carried out with an AcOEt/AcOH mixture, 9/1 by volume. 230 mg of a white powder are collected.

NMR SPECTRUM

| Delta | Appearance | Protons | Assignment |
| --- | --- | --- | --- |
| 7–8.4 | m | 11 H | 5 NH<br>5 H ar<br>1 H of the thiazole |
| 3.5 | s | 3 H | OCH₃ |
| 1.25 | s | 9 H | C(CH₃)₃ |

EXAMPLE 3

Boc-Phe-(Pyr-3)Ala-Sta-Leu-Phe-OMe (SR 43064 and SR 43066)

1. Ethyl (R,S)-2-acetamido-2-ethoxycarbonyl-3-(pyridin-3-yl)propionate 48 g of diethyl acetamidomalonate are added to 11 g of a solution of sodium in 300 ml of EtOH, and then, while heating under reflux, 36 g of 3-chloromethylpyridine hydrochloride are added and the mixture is kept under reflux for 5 h. The EtOH is evaporated off, the residue is taken up with water, the mixture is extracted and the extract is dried, concentrated and chromatographed on silica. Elution with a $CH_2Cl_2$/AcOEt mixture, 60/40 by volume, gives 23 g of the expected compound.

2. (R,S)-(Pyr-3)Ala.2HCl 15 g of the previous diester are heated under reflux in 200 ml of 5N HCl for 5 h. The mixture is concentrated to dryness, EtOH is added and the mixture is evaporated. The process is repeated until the dihydrochloride recrystallizes: 15 g.

3. (R,S)-Boc-(Pyr-3)Ala 1 g of the previous dihydrochloride is dissolved in a mixture of equal volumes of water and dioxane. 350 mg of sodium hydroxide and 1 g of $(Boc)_2O$ are added and the mixture is then stirred overnight at RT. The dioxane is evaporated off, water is added and the medium is neutralized with 8 g of amberlite CG 120 1 (acid form), stirred for 1 h at RT and then transferred to a column containing 8 g of the same resin. Elution is carried out with distilled water until the pH reaches 5 and then with a 4% solution of ammonia in distilled water. The eluates are concentrated. 0.69 g of the expected product is collected.

4. Boc-(Pyr-3)Ala-Sta-OMe

A mixture of 465 mg of Sta-OMe.TFA and 500 mg of Boc-(Pyr-3)Ala is stirred for 3 days at RT in 10 ml of acetonitrile in the presence of 780 mg of Bop, the medium being kept at about pH 7 by the addition of DIPEA. The mixture is then evaporated to dryness, water is added, the mixture is extracted with AcOEt and the extract is washed with a solution of $Na_2CO_3$, water and an aqueous solution of sodium chloride and then dried over $MgSO_4$ and evaporated to dryness. The residue is chromatographed on silica gel by elution with a $CH_2Cl_2$/AcOEt mixture, 1/9 by volume, which successively elutes:

the less polar A isomer: 150 mg;
the more polar B isomer: 180 mg.

5. Leu-Phe-OMe

This dipeptide is prepared by the coupling process described in the previous examples.

6. Boc-(Pyr-3)Ala-Sta-Leu-Phe-OMe

This compound is first prepared from the A isomer isolated in step 2. 200 mg of this A isomer are hydrolyzed at RT for 1 h in a mixture of equal volumes of water and dioxane. The mixture is partially evaporated under reduced pressure at RT, a trace of HCl is added to bring the pH to about 4, the mixture is then evaporated to dryness and the residue is dried in vacuo. It is taken up in 10 ml of acetonitrile; 200 mg of Leu-Phe-OCH_3.TFA and 230 mg of Bop are added and the reaction medium is kept for 18 h at about pH 7 by the addition of DIPEA. It is then evaporated to dryness, an aqueous solution of bicarbonate is added and the mixture is extracted with AcOEt. The organic phase, washed with water and an aqueous solution of sodium chloride and then dried over $MgSO_4$, yields the crude peptide after evaporation. This is purified by chromatography on silica gel using $CH_2Cl_2$/AcOEt, ¼ by volume, as the eluent. This gives 399 mg of product.

7. SR 43066

197 mg of the previous compound are brought into contact with 5 ml of TFA at 0° C. for 20 min, the solvent is then evaporated off and the salt obtained is dried in vacuo. The residue is suspended in $CH_2Cl_2$ and neutralized with DIPEA. A solution of 110 mg of Boc-Phe-ONp and 45 mg of HOBt is $CH_2Cl_2$ is added; the mixture is then stirred for 18 h at RT, the pH being kept at about 7 by the addition of DIPEA. The mixture is evaporated to dryness, an aqueous solution of carbonate is added and the mixture is extracted with AcOEt. After washing several times with water and drying over $MgSO_4$, the residue is chromatographed on silica gel (eluent: AcOEt). This gives 150 mg of SR 43066.

8. SR 43064

Starting from the B isomer isolated in step 4, the procedure of steps 4 and 5 is followed in order to prepare SR 43064.

NMR SPECTRUM OF SR 43066

| Delta | Appearance | Protons | Assignment |
|---|---|---|---|
| 6.80 | d, J = 8 Hz | 1 H | NH—Boc |
| 4.84 | d, J = 4 Hz | 1 H | OH (Sta) |
| 3.50 | s | 3 H | $OCH_3$ |
| 2.16-2.05 | m | 2 H | $CH_2$—CO (Sta) |
| 1.20 | s | 9 H | $(CH_3)_3C$ |

NMR SPECTRUM OF SR 43064

| Delta | Appearance | Protons | Assignment |
|---|---|---|---|
| 6.85 | d, J = 8 Hz | 1 H | NH—Boc |
| 4.83 | d, J = 4 Hz | 1 H | OH (Sta) |
| 3.50 | s | 3 H | $OCH_3$ |
| 2.10-1.95 | m | 2 H | $CH_2CO$ (Sta) |
| 1.21 | s | 9 H | $(CH_3)_3C$ |

EXAMPLE 4

Boc-Phe-(Pyr-4)Ala-Sta-Leu-Phe-OMe (SR 43065 and SR 43144)

1. Boc-(Pyr-4)Ala-Sta-OMe

By following the procedure of the previous example, Boc-(Pyr-4)Ala is prepared first and this product is then coupled with Sta-OMe.TFA. 2 isomers are isolated successively by chromatography:

the less polar A isomer;
the B isomer.

2. SR 43065

This compound is obtained from the A isomer by following the procedure of the previous example.

3. SR 43144

This compound is obtained from the B isomer by following the procedure of the previous example.

NMR SPECTRUM OF SR 43065

| Delta | Appearance | Protons | Assignment |
|---|---|---|---|
| 6.82 | d, J = 8 Hz | 1 H | NH—Boc |
| 4.85 | d, J = 4 Hz | 1 H | OH (Sta) |
| 3.50 | s | 3 H | OCH$_3$ |
| 2.10–2.07 | m | 2 H | CH$_2$CO (Sta) |
| 1.21 | s | 9 H | (CH$_3$)$_3$C |

NMR SPECTRUM OF SR 43144

| Delta | Appearance | Protons | Assignment |
|---|---|---|---|
| 6.87 | d, J = 8 Hz | 1 H | NH—Boc |
| 4.85 | d, J = 4 Hz | 1 H | OH (Sta) |
| 3.50 | s | 3 H | OCH$_3$ |
| 2.10–2.00 | m | 2 H | CH$_2$CO (Sta) |
| 1.23 | s | 9 H | (CH$_3$)$_3$C |

EXAMPLE 5

Boc-Phe-(Pyr-2)Ala-Sta-Leu-Phe-OMe (SR 43150 and SR 43151)

1. (R,S)-Boc-Phe-(Pyr-2)Ala 1 g of pyridin-2-ylalanine dihydrochloride and 1.65 g of Boc-Phe-ONp are stirred for 48 h at RT in 30 ml of a DMF/dioxane mixture, ½ by volume, in the presence of 2.5 ml of triethylamine. A small quantity of insoluble material is filtered off, the solution is evaporated to dryness and the residue is chromatographed on silica gel. A CHCl$_3$/MeOH/NH$_4$OH mixture (84/15/5 by volume) elutes the dipeptide in the form of a water-soluble foam. Yield: 58%.

2. Boc-Phe-(Pyr-2)Ala-Sta-OMe 880 mg of Bop and DIPEA are added to 808 mg of the previous product in CH$_2$Cl$_2$ at 0° C.; after a contact time of 15 min, 600 mg of Sta-OMe.TFA are then added and the pH is brought to about 6–7 by the addition of DIPEA. The mixture is stirred for 4 days at RT and then evaporated to dryness, an aqueous solution of carbonate is added and the mixture is extracted with AcOEt. After washing with water and an aqueous solution of sodium chloride, an oil is isolated. 850 mg are chromatographed on silica gel and the following are isolated successively by elution with AcOEt:
the less polar tripeptide, A, homogeneous in TLC;
the more polar tripeptide, B, containing 30% of A.

3. SR 43150

This compound is obtained from the A isomer by following the method described in Example 3.

4. SR 43151

This compound is obtained from the B isomer and contains 30 to 40% of SR 43150 after purification.

NMR SPECTRUM OF SR 43150

| Delta | Appearance | Protons | Assignment |
|---|---|---|---|
| 6.86 | d, J = 8 Hz | 1 H | NH—Boc |
| 4.76 | d, J = 4 Hz | 1 H | OH (Sta) |
| 3.50 | s | 3 H | OCH$_3$ |
| 2.13–2.07 | m | 2 H | CH$_2$CO (Sta) |
| 1.22 | s | 9 H | (CH$_3$)$_3$C |

EXAMPLE 6

Boc-Phe-Met(O$_2$)-Sta-Ala-Sta-OMe (SR 42845)

1. Z-Ala-Sta-OMe 1.44 g of H-Sta-OMe.TFA, 595 mg of NEM, 2.06 g of Z-Ala-OTcp and 1.29 g of HOBt are dissolved in 35 ml of DMF at room temperature. The pH is adjusted to 6–7 to pH paper with NEM if necessary and the mixture is stirred at RT for 48 h. The DMF is evaporated off in a water bath at 40° under a pressure of 0.01 mm of mercury. The residual oil is taken up in 50 ml of AcOEt and the mixture is washed successively with 5% KHSO$_4$—K$_2$SO$_4$ solution, NaCl/H$_2$O, 5% NaHCO$_3$ solution and NaCl/H$_2$O and dried over MgSO$_4$, and the solvent is evaporated off. The residue is taken up in ether and a solid appears. After one hour in a refrigerator, the solid is filtered off and dried.

Yield: 1.46 g (86%); m.p.: 117°–120° C.

2. H-Ala-Sta-OMe 1.46 g of Z-Ala-Sta-OMe are dissolved in 20 ml of MeOH, 1.03 g of ammonium formate are then added at RT, the mixture is stirred until a solution forms, 400 mg of 10% Pd/C are then added and the mixture is stirred for 5 min at RT. After 5 min, checking by TLC shows that the starting material has disappeared. The pH is 8 to pH paper. The whole mixture is filtered on celite and then the methanolic solution is filtered on a column of Amberlite IR 45 resin (OH) and the methanol is evaporated off. The residue is taken up in ether, the mixture is evaporated to dryness, the residue is then dissolved in CH$_2$Cl$_2$, the insoluble material is filtered off and the filtrate is evaporated to dryness to give a white powder.

Yield: 810 mg (75%); m.p.: 123°–134° C.

3. Boc-Sta-Ala-Sta-OMe 960 mg of H-Ala-Sta-OMe, 1 g of Boc-Sta-OH, 420 mg of HONSu and 750 mg of DCCI are dissolved successively in 50 ml of CH$_2$Cl$_2$ at RT. A white precipitate appears very quickly. The mixture is stirred at RT and, after 7 h, the DCU formed is filtered off and washed with CH$_2$Cl$_2$. The organic solution is washed successively with KHSO$_4$—K$_2$SO$_4$ (5% solution in H$_2$O) and NaHCO$_3$ (5% solution in H$_2$O). It is dried over MgSO$_4$ and filtered and the solvent is evaporated off. The product is solubilized in the minimum quantity of a chloroform/MeOH mixture (97.5/2.5, vol/vol) and deposited on the top of a column of silica gel; elution is carried out with the same mixture and the eluate is fractionated.

One batch of pure product and two batches of product for recycling under the same conditions are collected, giving an overall yield of 67%; m.p.: 95°–98° C.

4. H-Sta-Ala-Sta-OMe.TFA 200 mg of Boc-Sta-Ala-Sta-OMe are treated with 3.5 ml of TFA at 0° C. The mixture is stirred for 20 min at RT. Then, after concentration in vacuo, the oily residued is extracted by successively adding and concentrating anhydrous ether. This gives a white solid.

5. Boc-Met(O₂)-Sta-Ala-Sta-OMe 10 ml of DMF are added to the TFA salt obtained in the previous step (85 mg) and the pH is brought to 7 with NMM. 56.3 mg of Boc-Met($O_2$)—OH, 45.9 mg of HOBt and 45.4 mg of DCCI are introduced at −5° C. After a pH check, the mixture is stirred for 6 days at RT. 1 drop of AcOH is then added to the reaction mixture, this is stirred for 30 min and the DCU is then filtered off; the filtrate is taken up with an AcOH/butan-1-ol mixture, 75/25 by volume; the organic phase is washed successively with a saturated solution of NaCl, a 1% solution of $KHSO_4$, water, a 1% solution of $NaHCO_3$ and finally water. After drying and concentration, 120 mg of a white solid residue are recovered which are chromatographed on silica with AcOEt and then with an AcOEt/MeOH mixture, 9/1 by volume. This gives 60 mg of an amorphous white solid precipitated in hexane.

6. SR 42845

The 60 mg of product obtained in the previous step are added to 2 ml of TFA at 0° C. and the mixture is stirred for 20 min at RT. After concentration in vacuo, the oily residue is extracted by successively adding and concentrating anhydrous ether. 10 ml of $CH_2Cl_2$ are added to the white solid TFA salt thus obtained and the pH is brought to 7 with NMM. 33.4 mg of Boc-Phe-ONp and 14 mg of HOBt are then introduced; after a pH check, the mixture is stirred for 72 h at RT. The solution is diluted by the addition of $CH_2Cl_2$ and the organic phase is washed successively with a saturated solution of NaCl, a 1% solution of $KHSO_4$, water, a 1% solution of $NaHCO_3$ and then water. After drying and concentration, 58 mg of a solid residue are recovered which are chromatographed on silica with AcOEt and then with an AcOEt/MeOH mixture, 9/1 by volume. This gives 37 mg of an amorphous white solid precipitated in hexane.

NMR SPECTRUM

| Delta | Appearance | Protons | Assignment |
|---|---|---|---|
| 6.9–7.35 | 5 d, | | |
| 7.6–7.85 | J = 8 Hz | 5 H | 5 NH |
| 8.05 | | | |
| 7.1–7.25 | m | 5 H | H ar (Phe) |
| 4.8–5 | m | 2 H | OH (Sta) |
| 2.9 | s | 2 H | $CH_3$—$SO_2$ |
| 3.45 | s | 3 H | $OCH_3$ |
| 1.25 | s | 9 H | $C(CH_3)_3$ |

EXAMPLE 7

(R,S)-Boc-Phe-Hph-Sta-Ala-Sta-OMe (SR 42727)

1. Boc-Ala-Sta-OMe 4.1 g of H-Sta-OMe.TFA are introduced into 250 cm³ of $CH_2Cl_2$; 1.7 cm³ of NEM, 3.86 g of Boc-Ala-ONSu and 2 g of HOBt are added successively, the pH is then adjusted to 7 by the addition of NEM and the mixture is stirred overnight at RT. The mixture is washed twice with 500 cm³ of a saturated solution of $NaHCO_3$, twice with 500 cm³ of a $KHSO_4$—$K_2SO_4$ solution and with 500 cm³ of a saturated solution of NaCl and then dried over $MgSO_4$ and evaporated to dryness under reduced pressure.

Yield: 3.86 g (74.7%).

2. (R,S)-Hph.HCl

Homophenylalanine hydrochloride is prepared by the method described in J. Med. Chem., 1968, 11, 1258–1262.

3. (R,S)-Boc-Hph.HCl

In 50 ml of water, 2.8 g of the above hydrochloride are mixed with triethylamine to neutralize the solution to pH 7-8. 25 ml of dioxane, in which 3.12 g of tert.-butoxycarbonyl anhydride, (Boc)₂O, have been dissolved beforehand, are then added slowly at about 30°–40° C. and the mixture is then stirred overnight at RT. The resulting solution is diluted with water and washed twice with ether; AcOEt is added and the pH of the aqueous phase is then brought gradually to about 2.5-3 by the addition of 6N $H_2SO_4$. After 3 extractions with AcOEt and washing of the organic phase with a saturated aqueous solution of NaCl, the said organic phase is dried over $Na_2SO_4$ and then concentrated. 1 g of an amorphous white solid is recovered which precipitates in hexane.

4. (R,S)-Boc-Hph-Sta-OMe 434 mg of Boc-Sta-OMe are added to 5 ml of TFA at 0° C. and the mixture is stirred for 20 min at 0° C. After concentration in vacuo at RT, the oily residue is extracted by successively adding and concentrating anhydrous ether. 15 ml of $CH_2Cl_2$ are added to the white solid residue thus obtained, the pH is brought to 7 with NMM and 309.5 mg of DCCI, 229.5 mg of HOBt and 419 mg of previously obtained Boc-Hph.HCl are then added. The pH is checked (pH 7) and the mixture is stirred for 72 h at RT.

The insoluble material is filtered off and the methylene chloride filtrate is washed successively with a saturated solution of NaCl, a 1% solution of $KHSO_4$, water, a 1% solution of $NaHCO_3$ and water. After drying and concentration, 900 mg of an oily residue are obtained which are chromatographed on fine silica with AcOEt. This gives 230 mg of an amorphous white solid precipitated in hexane.

5. (R,S)-Boc-Hph-Sta-Ala-Sta-OMe 182 mg of Boc-Ala-Sta-OMe obtained in step 1 are added to 4 ml of TFA at 0° C., the mixture is stirred for 30 min at 0° C. and the excess TFA is then concentrated; the oily residue is subsequently extracted by successively adding and concentrating anhydrous ether. A white residue remains, 10 ml of $CH_2Cl_2$ are added, the pH is brought to 7 with NMM and then 76.5 mg of HOBt, 103.2 mg of DCCI and 220 mg of the product obtained in step 4 are added. The pH is checked (7) and the mixture is stirred for 72 h at RT. The insoluble material is filtered off and the filtrate is then washed with a saturated solution of NaCl, a 1% solution of $KHSO_4$, water, a 1% solution of $NaHCO_3$ and water. After drying and concentration, 364 mg of a residue are recovered which are chromatographed on fine silica with AcOEt. This gives 190 mg of an amorphous white solid which is a mixture of isomers.

6. SR 42727

170 mg of the product obtained in the previous step are added to 3 ml of TFA at 0° C.; after stirring for 30 min at 0° C., the excess TFA is concentrated and the oily residue is extracted by successively adding and concentrating anhydrous ether. 10 ml of $CH_2Cl_2$ are added to the resulting white residue, followed by NMM to bring the pH to 7, and 96.6 mg of Boc-Phe-ONp and 38.3 mg of HOBt are then added; the pH is adjusted to 7 and the mixture is stirred for 120 h at RT.

The solution is diluted with CH$_2$Cl$_2$ and the organic phase is washed successively with a solution of NaCl, a 1% solution of KHSO$_4$, water, a 1% solution of NaHCO$_3$ and water. After drying and concentration, 300 mg of a residue are recovered which are chromatographed on fine silica with AcOEt and then with an AcOEt/MeOH mixture, 9/1 by volume. This gives 170 mg of an amorphous white solid. This is the expected product (SR 42727) in the form of a mixture of isomers with respect to Hph.

NMR SPECTRUM

| Delta | Appearance | Protons | Assignment |
|---|---|---|---|
| 7–8.1 | m | 15 H | 5 NH |
|  |  |  | 10 H ar |
|  |  |  | (Phe, Hph) |
| 4.75 and | d, J = 4 Hz | 2 H | 2 OH (Sta) |
| 4.9 | J = 4 Hz |  |  |
| 3.5 | s | 3 H | OCH$_3$ |
| 1.25 | s | 9 H | C(CH$_3$)$_3$ |

EXAMPLE 8

Boc-Phe-(piMe)His-Sta-Ala-Sta-OMe (SR 43061)

This product is prepared from histidine protected by 2 Boc groups, one being on the amine group and the other on the tele nitrogen of the histidine:

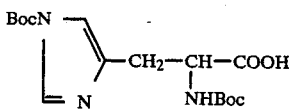

1. Bis(Boc)His-Sta-OMe 3.7 g of Boc-Sta-OMe are reacted with 15 ml of TFA at between 0° C. and +5° C. for 20 min. The mixture is concentrated, the concentrate is taken up 3 times with anhydrous ether and the mixture is concentrated to minimum volume. The TFA salt obtained is placed in 150 ml of CH$_2$Cl$_2$ and the pH is brought to 7 using DIPEA, with cooling. 6.6 g of Bis-Boc-His in the form of the DCHA salt are then added, the pH is brought to 7 with DIPEA, 6.3 g of Bop are added and the mixture is stirred for 3 days at RT and at pH 7. It is washed with an aqueous solution of sodium chloride, an aqueous solution of bicarbonate and then water, dried and concentrated. By chromatography on silica with AcOEt as the eluent, 7.8 g of a white powder are collected.

2. Boc-Phe-(piMe)His-Sta-OH

A mixture of 1 g of the product obtained in the previous step, 10 ml of anhydrous DMF and 5 ml of methyl iodide is heated under gentle reflux; after standing for 48 h, it is concentrated with a vacuum pump. When the concentrate is taken up with anhydrous ether, a yellow gum is obtained which hardens in AcOEt and solidifies in anhydrous ether. It is filtered off and dried with a gun. The solidified part and the concentrated mother liquors are added to 20 ml of TFA at 0° C. The mixture is stirred for 20 min, concentrated, treated 3 times with anhydrous ether and concentrated to minimum volume. The TFA salt obtained is dissolved in 25 ml of CH$_2$Cl$_2$ and the pH is brought to 7 with NMM. 724.5 mg of Boc-Phe-ONp and 299 mg of HOBt are added and the mixture is stirred for 4 days at RT. It is washed with an aqueous solution of sodium chloride, an aqueous solution of bicarbonate and then water, dried and concentrated. By chromatography on silica and elution with AcOEt/MeOH, 8/2 by volume, 2 polar fractions solidified in anhydrous ether are collected. This gives 639 mg of product. A saponification is then carried out starting from 300 mg to which 13 ml of MeOH, 2 ml of water and 167 mg of hydrated barium hydroxide are added, followed after 1 h by 84 g of hydrated barium hydroxide. TLC shows that the ester has disappeared. Small pieces of solid carbon dioxide are added until the pH drops below 7, the mixture is filtered on celite, the material on the filter is rinsed with methanol and the filtrate is concentrated; the residue is taken up with the minimum quantity of warm MeOH, the mixture is filtered and the filtrate is concentrated to give 248 mg of a white powder.

3. SR 43061

The compound obtained in the previous step is coupled with Boc-Ala-Sta-OMe by the methods described above.

NMR SPECTRUM

| Delta | Appearance | Protons | Assignment |
|---|---|---|---|
| 6.9, 7.4, |  |  |  |
| 7.6, 7.8, | 5 d, |  |  |
| 8.05 | J = 8 Hz | 5 H | NH |
| 7.1–7.25 | m | 5 H | 5 H ar (Phe) |
| 6.7, 7.4 | 2 s | 2 H | 2 H im |
| 3.5 | s | 3 H | OCH$_3$ |
| 3.55 | s | 3 H | (piCH$_3$)His |
| 1.25 | s | 9 H | C(CH$_3$)$_3$ |

EXAMPLE 9

Boc-Phe-(tauMe)His-Sta-Ala-Sta-OMe (SR 43062)

1. (tauMe)His-OH is prepared by the method described in J. R. Neth., Chem. Soc., 1978, 97, 293–295.

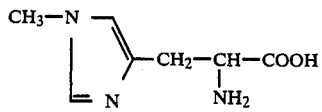

2. (tauMe)His-OMe.2HCl 4.5 g of the dihydrochloride of the above product are dissolved in 50 ml of MeOH; the solution is saturated with HCl gas at 10°–15° C. and then stirred at RT for 72 h. It is concentrated to dryness and the residue is taken up twice with ether and then with acetone; it crystallizes and 4 g of crystals are filtered off.

3. Boc-Phe-(tauMe)His-OMe 508 mg of the above product are placed in 25 ml of CH$_2$Cl$_2$ and the pH is brought to 7 by the addition of DIPEA. 772 mg of Boc-Phe-ONp and 306 mg of HOBt are added. After stirring for 2 days at RT, the mixture is washed with iced water and then dried and concentrated. By chromatography on silica and elution with an AcOEt/MeOH mixture, 9/1 by volume, 849 mg of the expected product are collected.

4. Boc-Phe-(tauMe)His 768 mg of the above product are dissolved in 33 ml of MeOH and 5 ml of water, to which 561 mg of hydrated barium hydroxide are added. After 1 h, 280 mg of barium hydroxide are added and the mixture is stirred for a further 1 h. Small pieces of solid carbon dioxide are then added until the pH is below 7, the mixture is then filtered on celite, the material on the filter is rinsed with MeOH and the filtrate is concentrated. The concentrate is taken up with MeOH, the small quantity of insoluble material is filtered off and the filtrate is concentrated. The concentrate is taken up with ether and the mixture is then filtered to give 634 mg of a white product.

5. H-Sta-Ala-Sta-OMe.TFA

This is prepared from 130 mg of Boc-Sta-Ala-Sta-OMe by the method described in Example 1.

6. Boc-Phe-(tauMe)His-Sta-Ala-Sta-OMe

The previously obtained TFA salt is placed in 10 ml of $CH_2Cl_2$ and DIPEA is added to bring the pH to 7; 124 mg of Bop and 104 mg of the product obtained in step 4 are then added, followed by 3 ml of anhydrous DMF, and the mixture is stirred for 72 h at pH 7. It is washed with an aqueous solution of sodium chloride and then with a dilute solution of bicarbonate and with water, dried and concentrated. The concentrate is chromatographed on silica by eluting with an AcOEt/MeOH mixture, 9/1 by volume. A fraction of 80 mg of a white product is isolated.

NMR SPECTRUM

| Delta | Appearance | Protons | Assignment |
|---|---|---|---|
| 7.0, 7.3, 7.4, 7.95, 8.1 | 5 d, J = 8 Hz J = 10 Hz J = 6 Hz J = 6 Hz J = 8 Hz | 5 H | 5 NH |
| 6.8 and 7.4 centered at | 2 s | 2 H | 2 H im |
| 4.95 | m | 2 H | 2 OH (Sta) |
| 7.1–7.3 | m | 5 H | 5 H ar (Phe) |
| 3.5 | d | 6 H | $OCH_3$ (tauMe)—His |
| 1.25 | s | 9 H | $C(CH_3)_3$ |

EXAMPLE 10

Boc-Phe-(cyclohexyl)Gly-Sta-Ala-Sta-OMe (SR 43091)

N-Boc-(2-alpha-cyclohexyl)glycine is prepared from L-alpha-phenylglycine by catalytic hydrogenation over Adams' catalyst ($PtO_2$). The methods described above are then followed in order to prepare SR 43091.

NMR SPECTRUM

| Delta | Appearance | Protons | Assignment |
|---|---|---|---|
| 6.9–7.85 centered at 7.2 | m | 5 H | 5 NH |
| | m | 5 H | 5 H ar |
| 4.8 and 4.95 | 2 d, J = 5 Hz J = 4 Hz | 2 H | 2 OH (Sta) |
| 3.5 | s | 3 H | $OCH_3$ |
| 1.25 | s | 9 H | $C(CH_3)_3$ |

EXAMPLE 11

Boc-Phe-(Pyr-3)Ala-Sta-Ala-Sta-OMe (SR 43429)

1. Ethyl 2-acetamido-2-ethoxycarbonyl-3-(pyridin-3-yl)propionate 48 g of diethyl acetamidomalonate are added to 11 g of a solution of sodium in 300 ml of EtOH, and then, while heating under reflux, 36 g of 3-chloromethylpyridine hydrochloride are added and the mixture is kept under reflux for 5 h. The EtOH is evaporated off, the residue is taken up with water, the mixture is extracted and the extract is dried, concentrated and chromatographed on silica. Elution with a $CH_2Cl_2$/AcOEt mixture, 60/40 by volume, gives 23 g of the expected compound.

2. (Pyr-3)Ala.2HCl 15 g of the previous diester are heated under reflux in 200 ml of 5N HCl for 5 h. The mixture is concentrated to dryness, EtOH is added and the mixture is evaporated. The process is repeated until the dihydrochloride recrystallizes: 15 g.

3. Boc-(Pyr-3)Ala 1 g of the previous dihydrochloride is dissolved in a mixture of equal volumes of water and dioxane. 350 mg of sodium hydroxide and 1 g of $(Boc)_2O$ are added and the mixture is then stirred overnight at RT. The dioxane is evaporated off, water is added and the medium is neutralized with 8 g of amberlite CG 120 l (acid form), stirred for 1 h at RT and then transferred to a column containing 8 g of the same resin. Elution is carried out with distilled water until the pH reaches 5 and then with a 4% solution of ammonia in distilled water. The eluates are concentrated. 0.69 g of the expected product is collected.

4. Boc-(Pyr-3)Ala-Sta-OMe

A mixture of 465 mg of Sta-OMe.TFA and 500 mg of Boc-(Pyr-3)Ala is stirred for 3 days at RT in 10 ml of acetonitrile in the presence of 780 mg of Bop, the medium being kept at about pH 7 by the addition of DIPEA. The mixture is then evaporated to dryness, water is added, the mixture is extracted with AcOEt and the extract is washed with a solution of $Na_2CO_3$, water and an aqueous solution of sodium chloride and then dried over $MgSO_4$ and evaporated to dryness. The residue is chromatographed on silica gel by elution with a $CH_2Cl_2$/AcOEt mixture, 1/9 by volume, which successively elutes:

the less polar A isomer: 150 mg;
the more polar B isomer: 180 mg.

5. SR 43429

The expected compound is obtained in the form of a pure isomer from the B isomer using the conventional coupling methods.

NMR SPECTRUM

| Delta | Appearance | Protons | Assignment |
|---|---|---|---|
| 8.41 | s | 1 H | H2 (Pyr) |
| 8.32 | d, J = 4 Hz | 1 H | H6 (Pyr) |
| 8.02–7.33 | m | 6 H | NHCO, H (Pyr) |
| 7.27–7.04 | m | 5 H | $C_6H_5$ |
| 6.87 | d, J = 8 Hz | 1 H | $NHCO_2$ |
| 4.97 | d, J = 4 Hz | 1 H | OH |
| 4.85 | d, J = 4 Hz | 1 H | OH |
| 4.64–3.90 | m | 3 H | CH alpha (Ala, Phe, (Pyr—3)Ala) |
| 3.90–3.67 | m | 4 H | CHNH, CHOH (Sta) |
| 3.50 | s | 3 H | $OCH_3$ |
| 3.10–2.47 | m | 4 H | $CH_2C_5H_4N$ $CH_2C_6H_5$ |
| 2.96–1.90 | m | 4 H | $CH_2CO$ (Sta) |
| 1.57–1.00 | m | 18 H | $(CH_3)_3C$, $CH_3$ (Ala) CH, CH (Sta) |
| 0.87–0.66 | m | 12 H | $CH_3$ (Sta) |

The following compounds were prepared using the same coupling methods:

| SR no. | Formula |
|---|---|
| 42823 | Boc—Phe—Phg—Sta—Ala—Sta—OMe |
| 42928 | Boc—Phe—Asn—Sta—Ala—Sta—OMe |
| 42939 | Boc—Phe—(Ph $CH_2O$)Ser—Sta—Ala—Sta—OMe |
| 42980 | Boc—Phe—Gln—Sta—Ala—Sta—OMe |
| 43075 | (R,S)—Boc—Phe—(thien-2-yl)Gly—Sta—Ala—Sta—OMe |
| 43266 | Boc—Phe—(Ph)Gln—Sta—Ala—Sta—OMe |
| 43281 | Boc—Phe—(Ph)Asn—Sta—Ala—Sta—OMe |
| 43297 | Boc—Phe—(($CH_3)_3$CO)Ser—Sta—Ala—Sta—OMe |
| 43365 | Boc—Phe—($CH_3CH_2O$)Ser—Sta—Ala—Sta—OMe |
| 43366 | Boc—Phg—Phg—Sta—Leu—Phe—OMe |
| 43391 | Boc—Phe—(tauEt)His—Sta—Ala—Sta—OMe |
| 43428 | Boc—Phe—(1-methylimidazol-2-yl)Ala—AHPPA—Ala—Sta—$OCH_3$ |
| 43554 | Boc—Phe—Cpg—Sta—Ala—Sta—OMe |
| 43555 | Boc—Phe—((Pyr-2)$CH_2O$)Ser—Sta—Ala—Sta—OMe |
| 43556 | Boc—Phe—(cyclohexyl)Ala—Sta—Ala—Sta—OMe |
| 43761 | iVa—Phe—(tauMe)His—Sta—Ala—Sta—OH |

These products are characterized by their NMR spectrum. CL NMR SPECTRUM OF SR 42823

| Delta | Appearance | Protons | Assignment |
|---|---|---|---|
| 7–8.3 | m | 15 H | 5 NH 10 H ar |
| 4.8 and 5 | 2 d, J = 4 Hz | 2 H | 2 OH (Sta) |
| 3.5 | s | 3 H | $OCH_3$ |
| 1.2 | s | 9 H | $C(CH_3)_3$ |

NMR SPECTRUM OF SR 42928

| Delta | Appearance | Protons | Assignment |
|---|---|---|---|
| 6.85–8.25 | m | 12 H | 5 NH 5 H ar $CONH_2$ |
| 5.8 and 5.9 | 2 d, J = 6 Hz | 2 H | OH (Sta) |
| 1.25 | s | 9 H | $C(CH_3)_3$ |

NMR SPECTRUM OF SR 42939

| Delta | Appearance | Protons | Assignment |
|---|---|---|---|
| 6.9–8.1 | m | 15 H | 5 NH 10 H ar |
| 4.85 and 4.95 | 2 d, J = 5 Hz | 2 H | OH (Sta) |
| 4.45 | s | 2 H | $OCH_2C_6H_5$ |
| 3.5 | s | 3 H | $OCH_3$ |
| 1.25 | s | 9 H | $C(CH_3)_3$ |

NMR SPECTRUM OF SR 42980

| Delta | Appearance | Protons | Assignment |
|---|---|---|---|
| 6.75–8 | m | 12 H | 5 NH 5 H ar $NH_2$ (Gln) |
| 4.85 and 4.95 | 2 d, J = 5 Hz | 2 H | OH (Sta) |
| 3.5 | s | 3 H | $OCH_3$ |
| 1.25 | s | 9 H | $C(CH_3)_3$ |

NMR SPECTRUM OF SR 43075

| Delta | Appearance | Protons | Assignment |
|---|---|---|---|
| 6.9–8.5 | m | 13 H | 5 NH 5 H ar 3 H of the thiophene |
| 4.8–4.9 | m | 2 H | OH (Sta) |
| 3.5 | s | 3 H | $OCH_3$ |
| 1.25 | s | 9 H | $C(CH_3)_3$ |

NMR SPECTRUM OF SR 43266

| Delta | Appearance | Protons | Assignment |
|---|---|---|---|
| 9.8 | s | 1 H | NH ($NHC_6H_5$) |
| 6.9–9.1 | m | 15 H | 5 NH 10 H ar |
| 4.85–5 | m | 2 H | OH (Sta) |
| 3.5 | s | 3 H | $OCH_3$ |
| 1.25 | s | 9 H | $C(CH_3)_3$ |

NMR SPECTRUM OF SR 43281

| Delta | Appearance | Protons | Assignment |
|---|---|---|---|
| 10.1 | s | 1 H | NH (NH—$C_6H_5$) |
| 6.95–8.4 | m | 15 H | 5 NH 10 H ar |
| 4.8 and | 2 d, | 2 H | 2 OH (Sta) |

-continued

| Delta | Appearance | Protons | Assignment |
|---|---|---|---|
| 4.95 | J = 6 Hz | | |
| 3.8 | s broad | 2 H | 2 H alpha (Sta) |
| 3.5 | s | 3 H | CH₃ ester |
| 1.25 | s | 9 H | C(CH₃)₃ |

NMR SPECTRUM OF SR 43297

| Delta | Appearance | Protons | Assignment |
|---|---|---|---|
| 7 to 7.85 | m | 10 H | 5 NH 5 ar |
| 4.6 to 5 | m | 2 H | OH (Sta) |
| 3.8 | s broad | 2 H | 2 H alpha (Sta) |
| 3.5 | s | 3 H | CH₃ ester |
| 1.25 | s | 9 H | Boc |
| 1.05 and 1 | 2 isomer peaks | 9 H | C(CH₃)₃ |

NMR SPECTRUM OF SR 43365

| Delta | Appearance | Protons | Assignment |
|---|---|---|---|
| 7.2<br>6.95<br>7.30<br>7.45<br>7.80<br>8.0 | m<br><br>5 d,<br>J = 8 Hz | 5 H<br><br>5 H | ar<br><br>NH |
| 4.8–4.95 | 2 d, J = 4 Hz | 2 H | OH (Sta) |
| 3.75<br>4.2<br>4.4 | 3 m | 4 H | 4 H alpha (Phe, Ser, Sta) |
| 3.5 | s | 3 H | OCH₃ |
| 3.35 | q | | OCH₂CH₃ |
| 1.25 | s | 9 H | C(CH₃)₃ |
| 1.0 | t | 3 H | OCH₂CH₃ |

NMR SPECTRUM OF SR 43391

| Delta | Appearance | Protons | Assignment |
|---|---|---|---|
| 6.8 to 8.2 | m | 12 H | 5 NH, 5 ar, 2 His |
| 4.95 | m | 2 H | OH (Sta) |
| 3.5 | s | 3 H | OCH₃ ester |
| 1.25 | s | 9 H | C(CH₃)₃ |

NMR SPECTRUM OF SR 43366

| Delta | Appearance | Protons | Assignment |
|---|---|---|---|
| 7.1 to 8.75<br>5.35 and<br>5.5 | m<br><br>2 d, J = 8 Hz | 15 H<br><br>2 H | 10 H C₆H₅, 5 NH<br>2 H alpha (Phg) |
| 5 | m | 1 H | OH (Sta) |
| 3.65 | m | 2 H | H alpha (Sta) |
| 3.5 | s | 3 H | OCH₃ ester |
| 1.35 | s | 9 H | C(CH₃)₃ |

NMR SPECTRUM OF SR 43428 (2 isomers: 7/3)

| Delta | Appearance | Protons | Assignment |
|---|---|---|---|
| 8.25–7.76 | m | 3 H | NHCO |
| 7.39 | d, J = 8 Hz | 1 H | NHCO |
| 7.25–7.00 | m | 10 H | C₆H₅ |
| 7.00–6.89 | m | 2 H | NHCO₂, H im |
| 6.89<br>5.71 | 2 s | 1 H | H im |
| 5.32–4.0 | m | 5 H | OH, H alpha (Ala, Phe, im) |
| 4.0–3.67 | m | 4 H | CHNH, CHOH (AHPPA, Sta) |
| 3.53<br>3.44 | 2 s | 3 H | N—CH₃ |
| 3.50 | s | 3 H | OCH₃ |
| 3.00–1.95 | m | 10 H | CH₂—C₆H₅, CH₂ im, CH₂CO (AHPPA, Sta) |
| 1.57–1.00 | m | 15 H | (CH₃)₃C, CH₃ (Ala), CH and CH₂ (Sta) |
| 0.77–0.69 | m | 6 H | CH₃ (Sta) |

NMR SPECTRUM OF SR 43554

| Delta | Appearance | Protons | Assignment |
|---|---|---|---|
| 6.92–7.89 | m including 4 d at 6.95, 7.37, 7.57, 7.89 ppm J = 6 Hz | 10 H | 5 NH (amides) 5 Ar (Phe) |
| 4.95<br>4.80 | 2 d<br>J = 4 Hz | 2 H | 2 OH (Sta) |
| 3.35–4.22 | m including s at 3.51 ppm (OCH₃ Sta) | 10 H | CH alpha (Phe) CH alpha (Cpg) 4 CH alpha (Sta) CH alpha (Ala) OCH₃ Sta OMe |
| 2.03–2.95 | m | 6 H | CH₂ (Phe) 2 CH₂—CO (Sta) |
| 0.68–1.6 | m including s at 1.20 ppm | 32 H | 4 CH₃ (Sta) CH₃ (Ala) C(CH₃)₃ 4 CH₂ (cyclopentyl) |

NMR SPECTRUM OF SR 43556

| Delta | Appearance | Protons | Assignment |
|---|---|---|---|
| 6.90–8.0 | m including 3 d at 6.93, 7.87, 7.96 J = 4 Hz | 10 H | 5 NH (amides) 5 Ar (Phe) |
| 4.92 and 4.83 | 2 d J = 4 Hz | 2 H | 2 OH (Sta) |
| 3.5–4.38 | m including s at 3.5 | 10 H | CH alpha (Phe) CH alpha (Ala) CH alpha ((cyclohexyl)Ala) 4 CH alpha (Sta) CH₃ (OMe) |
| 2–2.91 | m | 6 H | CH₂ (Phe) 2 CH₂CO (Sta) |
| 0.94–1.74 | m | 31 H | 3 CH₃ (Boc) 13 CH₂—C₅H₁₁ 2 CH₂—CH (Sta) CH₃ (Ala) |
| 0.71–0.94 | m | 12 H | 4 CH₃ (2 Sta) |

NMR SPECTRUM OF SR 43761

| Delta | Appearance | Protons | Assignment |
|---|---|---|---|
| 6.81–8.52 | m including | 12 H | 5 Ar; 5 NH; |

-continued

| Delta | Appearance | Protons | Assignment |
|---|---|---|---|
| | 3 d centered at 7.03, 8.26, 8.5 J = 8 Hz | including 3 H | 1 H (His) NH (amides) |
| | s at 7.4 | 1 H | H (His) |
| | s at 7.22 | 5 H | H Ar |
| | s at 6.81 | 1 H | H (His) |
| 5.13 | m | 1 H | OH (Sta) |
| 4.15–4.44 | m | 3 H | H alpha (Phe) H alpha (His) H alpha (Ala) |
| 3.58–3.78 | m | 4 H | Sta |
| 3.52 | s | 3 H | $CH_3$ (tauMe)-His |
| 2.63–3.04 | m | 4 H | $CH_2$ (Phe) $CH_2$ (His) |
| 0.97–2.11 | m | 19 H | 2 $CH_2CO$ (Sta) $CH_2$—CH (iVa) 2 $CH_2$—CH (Sta) $CH_3$ (Ala) |
| 0.55–0.82 | m | 16 H | 2 $CH_3$ (iVa) 4 $CH_3$ (Sta) |

The products according to the invention were studied for their therapeutic properties and especially their inhibitory action on enzymes. More particularly, the compounds were evaluated "in vitro" in terms of their inhibition of human plasma renin activity (PRA) and the results are superior to those obtained with the natural product, pepstatin.

I-METHOD

The method of evaluation is based on that of GUYENE (J. Clin. Endocrinol. Metab., 1976, 43, 1301) to the extent that the inhibition of PRA is evaluated from a human plasma pool rich in renin (15 to 20 mg of angiotensin I released per milliliter and per hour), incubated for 60 minutes at 37° C., in a phosphate buffer at pH 7.4, in the presence of increasing concentrations of the product to be studied.

Human plasma contains the substrate angiotensinogen and the enzyme renin. The angiotensin I released during the reaction is measured by radioimmunoassay using a kit: Plasma Renin Activity Kit from Travenol (no. CA 533553). An inhibitor of the conversion enzyme, phenylmethylsulfonyl fluoride (PMSF), is added to the incubation medium. The total incubation volume is 555 microliters divided up as follows:
- 420 microliters of human plasma
- 11 to 50 microliters of the product to be studied, at variable concentrations
- 119 to 80 microliters of phosphate buffer
- 5 microliters of PMSF.

A solution of acetic acid in methanol (19/1 by volume) and a solution of sodium hydroxide in methanol (2/1 by volume) are prepared. In a mixture of equal volumes of these 2 solutions, a 0.001M stock solution of the peptide is prepared. The subsequent dilutions of the peptide are then made up in the phosphate buffer.

The quantity of solvent present in a solution of the peptide at a concentration of less than 0.0001M does not interfere with the results.

II-RESULTS

The results are expressed as the dose of compound, evaluated in mol, which causes a 50% inhibition ($IC_{50}$) of the human plasma renin activity observed in the absence of inhibitor.

The results obtained with various products of the invention are given in the following table (I), which shows the $IC_{50}$ values of each molecule in terms of their inhibition of human plasma renin activity at pH 7.4. From 5 to 10 doses were required in order to determine these $IC_{50}$ values. Pepstatin, used as the reference substance, is always tested in parallel in each experiment. The results are expressed by their logarithmic value ($-\log IC_{50}$).

TABLE I

| Sr no. | Inhibition of human PRA- $-\log IC_{50}M$ pH 7.4 |
|---|---|
| Pepstatin | 4.92 |
| 42 823 | 7.03 |
| 42 926 | 6.40 |
| 42 928 | 5.92 |
| 42 939 | 6.76 |
| 42 980 | 6.50 |
| 43 059 | 5.52 |
| 43 064 | 6.50 |
| 43 075 | 6.60 |
| 43 144 | 5.88 |
| 43 150 | 5.21 |
| 41 151 | 6.66 |
| 43 281 | 5.85 |
| 43 297 | 5.67 |
| 43 365 | 6.95 |
| 43 391 | 7.19 |
| 43 428 | 6.16 |
| 43 429 | 6.38 |
| 43 554 | 7.43 |
| 43 555 | 6.50 |
| 43 556 | 6.31 |
| 43 761 | 6.82 |

The toxicity of the products according to the invention is compatible with their use in therapy.

What is claimed is:

1. A peptide derivative of formula (I):

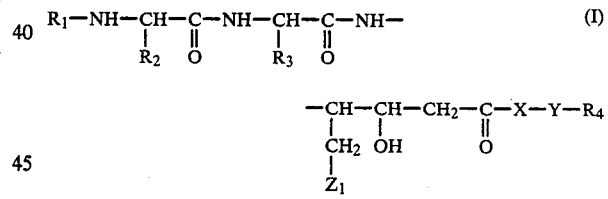

in which:
R$_1$ represents an alkylcarbonyl or alkoxycarbonyl group;
R$_2$ represents phenyl or benzyl;
R$_3$ represents:
 (a) phenyl, cyclopentyl, cyclohexyl, a thienyl unsubstituted or substituted by a methyl, a thiazolyl unsubstituted or substituted by a method, an imidazolyl unsubstituted or substituted by a methyl;
 (b) a methylene substituted by:
  a carboxyl esterified by a lower alkyl or a benzyl,
  a carbamoyl substituted by one or two alkyls or by a phenyl,
  a lower alkoxy, a benzyloxy, a pyridylmethyloxy,
  an imidazolyl substituted by a methyl, an ethyl or a trifluoromethyl, or
  a pyridyl; or
 (c) an ethylene substituted by:
  a phenyl, or a free carbamoyl or a carbamoyl substituted by one or two alkyls or by a phenyl;

$R_4$ represents a hydroxyl, a lower alkoxy, a benzyloxy or a free amino group or an amino group substituted by one or two lower alkyl groups;

$Z_1$ represents isopropyl, phenyl or cyclohexyl, respectively forming with the radical:

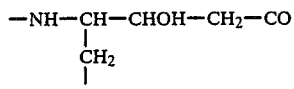

the residue of the amino acid statin, namely (3S,4S)-4-amino-3-hydroxy-6-methylheptanoic acid, of (3S,4S)-4-amino-3-hydroxy-5-phenylpentanoic acid (AHPPA) or of (3S,4S)-4-amino-5-cyclohexyl-3-hydroxypentanoic acid (ACHPA); and X-Y is a dipeptide which is Ala-Sta, Ala-Leu, Leu-Phe, or Val-Sta;

and pharmaceutically acceptable salts thereof with mineral or organic acids or alkali metals or alkaline earth metals.

2. A peptide derivative as claimed in claim 1, in which $R_1$ is tertiobutyloxy carbonyl or isovaleryl.

3. A peptide derivative as claimed in claim 1, in which $R_2$ is benzyl.

4. A peptide derivative of formula:
Boc-Phe-(tau Me)His-Sta-Ala-Sta-OMe.

5. A peptide derivative as claimed in claim 1, wherein the residue —NH—CH($R_3$)—CO— represents the residue (tauMe)His.

6. A pharmaceutical composition for the treatment of arterial tension which comprises as active ingredient an effective amount for the treatment of arterial tension of a product as claimed in claim 1 mixed with a pharmaceutical excipient.

7. A pharmaceutical composition as claimed in claim 6 in dosage unit form and wherein the dosage unit contains from 1-100 mg of the active ingredient.

* * * * *